United States Patent [19]

Edwards et al.

[11] Patent Number: 5,434,145
[45] Date of Patent: Jul. 18, 1995

[54] N-ALKYTHIO POLYAMINE DERIVATIVES AS RADIOPROTECTIVE AGENTS

[75] Inventors: Michael L. Edwards, Cincinnati; Ronald D. Snyder, Loveland, both of Ohio

[73] Assignee: Merrell Dow Pharmaceuticals Inc., Cincinnati, Ohio

[21] Appl. No.: 323,472

[22] Filed: Oct. 14, 1994

Related U.S. Application Data

[63] Continuation of Ser. No. 180,007, Jan. 11, 1994, abandoned, which is a continuation of Ser. No. 69,302, May 26, 1993, abandoned.

[51] Int. Cl.⁶ .................. A61K 31/66; A61K 31/13; C07F 9/165; C07C 211/14
[52] U.S. Cl. ................... 514/108; 514/114; 514/674; 558/158; 558/166; 564/512
[58] Field of Search .......... 514/108, 114, 674; 558/158, 166; 564/512

[56] References Cited

U.S. PATENT DOCUMENTS

| | | | |
|---|---|---|---|
| 2,653,977 | 9/1953 | Craig et al. | 564/367 |
| 2,951,092 | 8/1960 | Sowinski et al. | 564/47 |
| 3,892,824 | 7/1975 | Piper . | |
| 5,109,024 | 4/1992 | Prakash et al. | 514/674 |
| 5,217,964 | 6/1993 | Edwards et al. | 514/104 |
| 5,342,945 | 8/1944 | Bergeron | 544/296 |

FOREIGN PATENT DOCUMENTS

| | | |
|---|---|---|
| 0349224 | 1/1990 | European Pat. Off. . |
| 0497202 | 8/1992 | European Pat. Off. . |
| 9317689 | 9/1993 | WIPO . |

OTHER PUBLICATIONS

Piper, J. R. *J. Org. Chem.* 1968, 33(2), 636–42.
Edwards, et al., J. of Medicinal Chem. 34(2): 569–574 (1991).
Edwards, et al., J. of Medicinal Chem. 34(8): 2414–2420 (1991).
Edwards, et al., J. of Medicinal Chem 33(5): 1369–1375 (1990).

*Primary Examiner*—Robert W. Ramsuer
*Assistant Examiner*—Michael G. Ambrose
*Attorney, Agent, or Firm*—Louis J. Wille; Nelsen L. Lentz

[57] ABSTRACT

The present invention relates to certain polyamine thiols which are useful as radioprotective agents.

19 Claims, No Drawings

N-ALKYTHIO POLYAMINE DERIVATIVES AS RADIOPROTECTIVE AGENTS

CROSS-REFERENCE TO RELATED APPLICATIONS

This is a continuation of application Ser. No. 08/180,007, filed Jan. 11, 1994, now abandoned, which is a continuation of application Ser. No. 08/069,302, filed May 26, 1993, now abandoned, which is herein incorporated by reference.

BACKGROUND OF THE INVENTION

Radioprotective agents, also known as radioprotectors, are defined as agents which protect cells or organisms from deleterious cellular effects of exposure to ionizing radiation. These deleterious cellular effects include damage to cellular DNA, such as DNA strand break, disruption in cellular function, cell death, tumor induction and the like. The mechanism of this protective effect may at least partially be due to radical scavenging properties of the radioprotective agents.

The potential utility of these agents in protecting against exposure to environmental radiation, as well as in cancer radiation therapy, has long been recognized. These agents, administered prior to or during exposure, would eliminate or reduce the severity of deleterious cellular effects caused by exposure to environmental ionizing radiation such as resulting from a nuclear explosion, a spill of radioactive material, close proximity to radioactive material and the like.

In addition, these agents are believed to provide a selective protection of normal cells, and not of cancer cells, during cancer radiation therapy. For example, these agents, administered to the cancer patient prior to or during radiation therapy, will be absorbed by normal, non-cancer cells to provide a protective effect. However, the radioprotective agents will not be absorbed to the same extent by tumor cells due to the poor vascularity associated with the tumor. Therefore, the radioprotective agents would provide a selective protective effect on the normal cells as compared to tumor cells and would eliminate or reduce the severity of deleterious cellular effects of radiation therapy on normal cells. Furthermore, some radioprotective agents may act as prodrugs and require activation by cellular enzymatic processes which are not fully operative in the cancer cell. These agents, even if absorbed in a similar concentration in normal and cancer cells, will only be activated in cells with normal enzymatic processes and not in cancer cells. These prodrug radioprotective agents would be activated to provide a selective protective effect only in normal cells and would thus eliminate or reduce the severity of deleterious cellular effects of radiation therapy on normal cells.

Furthermore, certain radioprotective agents provide a selective protection against deleterious cellular effects in normal cells caused by certain DNA-reactive agents such as cisplatin, cyclophosphamide, diethylnitrosoamine, benzo(a)pyrene, carboplatin, doxorubicin, mitomycin-C and the like. Many of these DNA-reactive agents are chemotherapeutic agents useful in cancer therapy. Radioprotective agents are useful in eliminating or reducing the severity of deleterious effects in normal cells caused by exposure to these DNA-reactive agents, such as during cancer therapy with DNA-reactive chemotherapeutic agents.

In addition, certain radioprotective agents provide a selective protection against therapy-induced secondary tumor induction [See Grdina et al., Pharmac. Ther. 39, 21 (1988)]. Radiation and chemotherapy provide effective treatments for a variety of neoplastic disease states. Unfortunately, these treatments themselves are oftentimes mutagenic and/or carcinogenic and result in therapy-induced secondary tumor induction. For example, patients treated for Hodgkin's disease appear to exhibit a relatively high risk for therapy-induced acute myelogenous leukemia and non-Hodgkin's lymphoma. Radioprotective agents provide selective protection against deleterious cellular effects, such as tumor induction, caused by radiation therapy or chemotherapy with a DNA-reactive chemotherapeutic agent. Radioprotective agents are thus useful in eliminating or reducing the risk of secondary tumor induction brought about by radiotherapy or chemotherapy.

Radioprotective agents thus are useful in eliminating or reducing the severity of deleterious cellular effects in normal cells caused by environmental exposure to ionizing radiation, cancer radiation therapy and treatment with DNA-reactive chemotherapeutic agents. See generally, Weiss and Simic, Pharmac. Ther. 39, 1 (1988).

The prototypical radioprotective agent, developed by the Antiradiation Drug Development Program at the Walter Reed Army Institute of Research, is WR-2721, or S-2(3-aminopropylamino)ethylphosphorothioic acid, which has the structure

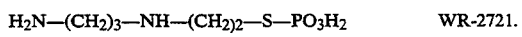
$$H_2N-(CH_2)_3-NH-(CH_2)_2-S-PO_3H_2 \quad\quad WR\text{-}2721.$$

Other known radioprotective agents are WR-1065, thought to be a metabolite of WR-2721, which has the structure

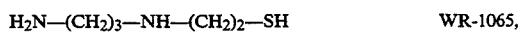
$$H_2N-(CH_2)_3-NH-(CH_2)_2-SH \quad\quad WR\text{-}1065,$$

and WR-151,327, which has the structure

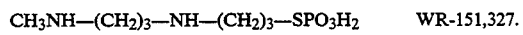
$$CH_3NH-(CH_2)_3-NH-(CH_2)_3-SPO_3H_2 \quad\quad WR\text{-}151,327.$$

SUMMARY OF THE INVENTION

The present invention provides novel radioprotective agents of the formula (I)

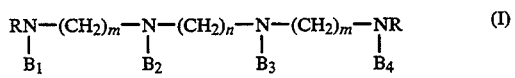
$$\underset{B_1}{RN}-(CH_2)_m-\underset{B_2}{N}-(CH_2)_n-\underset{B_3}{N}-(CH_2)_m-\underset{B_4}{NR} \quad\quad (I)$$

wherein
m is an integer from 2 to 4,
n is an integer from 3 to 10,
R is $C_2$–$C_6$ alkyl and
$B_1$, $B_2$, $B_3$ and $B_4$ are each independently H, $-CH_2CH_2SH$ or $-CH_2CH_2SPO_3H_2$;
and the pharmaceutically acceptable addition salts thereof; with the proviso that at least one of $B_1$, $B_2$, $B_3$ or $B_4$ is other than H.

The present invention further provides novel radioprotective agents of the formula (II)

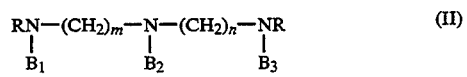
$$\underset{B_1}{RN}-(CH_2)_m-\underset{B_2}{N}-(CH_2)_n-\underset{B_3}{NR} \quad\quad (II)$$

wherein m is an integer from 2 to 4,
n is an integer from 3 to 10,
R is $C_2$–$C_6$ alkyl and
$B_1$, $B_2$ and $B_3$ are each independently H, —$CH_2CH_2SH$ or —$CH_2CH_2SPO_3H_2$;
and the pharmaceutically acceptable addition salts thereof; with the proviso that at least one of $B_1$, $B_2$ or $B_3$ is other than H.

In addition, the present invention provides a method of protecting mammalian cells from deleterious cellular effects caused by exposure to ionizing radiation or to a DNA-reactive agent comprising contacting said cells with a protective amount of a compound of formula (I) or (II).

The present invention also provides a method of protecting non-cancer cells of a human from deleterious cellular effects caused by exposure to ionizing radiation or by exposure to a DNA-reactive agent comprising administering to said human a protective amount of a compound of formula (I) or (II).

The present invention further provides a method of treating a patient in need of radiation therapy, or in need of chemotherapy with a DNA-reactive chemotherapeutic agent, comprising administering to said patient a protective amount of a compound of formula (I) or (II).

DETAILED DESCRIPTION OF THE INVENTION

As used herein, the following terms have the meanings as indicated below:

(1) the term "$C_2$–$C_6$ alkyl" refers to a saturated straight or branched chain hydrocarbyl radical of one to six carbon atoms. Included within the scope of this term are ethyl, n-propyl, isopropyl, n-butyl, isobutyl, sec-butyl, t-butyl, n-pentyl, n-hexyl, 1,1-dimethylpropyl, 3,3-dimethylpropyl, 1-methylbutyl, 2-methylbutyl and the like.

2) The term "Ts" refers to a rosylate functionality of the formula:

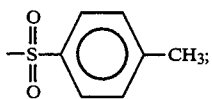

3) The term "Et" refers to an ethyl functionality of the formula:

—$CH_2$—$CH_3$

4) The term "Pr" refers to a propyl functionality of the formula:

—$CH_2$—$CH_2$—$CH_3$

5) The term "Bu" refers to a butyl functionality of the formula:

—$CH_2$—$CH_2$—$CH_2$—$CH_3$

6) The term "halogen" or "halo" refers to a chlorine, bromine or iodine atom.

7) The term "pharmaceutically acceptable addition salts" is intended to apply to any non-toxic organic or inorganic acid addition salt of the base compounds represented by Formula (I) or (II). Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methanesulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The polyamine derivatives of formula (I) can be prepared utilizing techniques well known in the art. The choice of any specific route of preparation is dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (I).

The following reaction schemes are illustrative of the pathways by which the compounds of formula (I) may be made. All substituents, unless otherwise indicated, are as previously defined. The reagents and starting materials are readily available to one of ordinary skill in the art. Preparation of starting material for use in Scheme II is described in Scheme I.

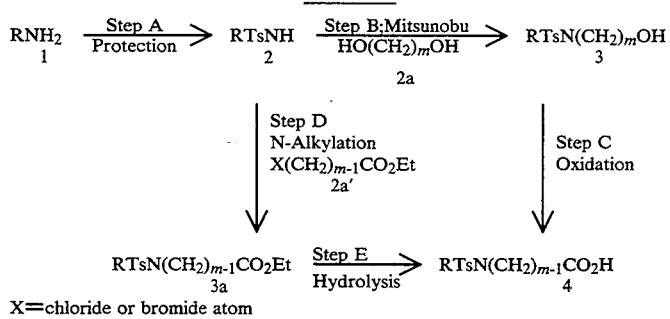

In Scheme I, step A the primary amine (1) is protected as the rosylate derivative described by structure (2) under conditions well known in the art as described in European Patent Publication No. 0 349 224 published Mar. 1, 1990.

For example the primary amine (1) is dissolved in a mixture of dichloromethane and 10% sodium hydroxide and cooled to 0° C. To the stirring solution is added dropwise an excess of p-toluenesulfonyl chloride. After approximately 1 hour the reaction is warmed to room temperature and allowed to stir for about 2 days. The reaction is neutralized with 0.5N hydrochloric acid and extracted with a suitable organic solvent, such as methylene chloride. The organic phase is rinsed with water, brine, dried over anhydrous sodium sulfate, filtered and concentrated under vacuum to provide the protected secondary amine (2).

In step B the protected secondary amine (2) is subjected to a Mitsunobu reaction utilizing an appropriately substituted diol (2a) to provide the primary alcohol described by structure (3).

For example, the protected secondary amine (2) is dissolved in a suitable organic solvent, such as tetrahydrofuran and treated with one equivalent of triphenylphosphine. This is then treated with one equivalent of the appropriately substituted diol (2a) followed by treatment with one equivalent of diethyl azodicarboxylate. This is allowed to stir at about 25° C. from 4 to about 18 hours. The product is isolated by extractive methods well known in the art, such as extraction into methylene chloride, rinsing with water, brine, drying over anhydrous sodium sulfate, filtering and concentration under vacuum. The residue is purified by techniques well known in the art, such as flash chromatography utilizing silica gel and a suitable eluent mixture, such as methanol/methylene chloride to provide the primary alcohol (3).

In step C the primary alcohol (3) is oxidized under conditions well known and appreciated in the art of chemistry as described generally by March, Advanced Organic Chemistry: Reactions, Mechanisms and Structure, McGraw-Hill Book Company, 2nd Ed., 1977, 1107–1108, to provide the carboxylic acid described by structure (4).

For example, the primary alcohol (3) is dissolved in acetone at 0° C. and a slight excess of Jones reagent (Bowden, K. et al. *J. Chem. Soc.*, 39, 1946) is added dropwise. The reaction is allowed to stir for 1 to 4 hours at 0° C. Isopropanol is then added and the reaction is filtered through diatomaceous earth which is rinsed with several portions of acetone and methylene chloride. The filtrate is concentrated under vacuum and the residue purified by techniques well known in the art, such as flash chromatography utilizing silica gel and a suitable eluent mixture, such as methanol/methylene chloride to provide the carboxylic acid (4).

Alternatively the carboxylic acid can be prepared following steps D and E in Scheme I starting with the protected secondary amine (2).

In step D the protected secondary amine (2) is N-alkylated with the appropriately substituted ethyl halocarboxylate (2a') to provide the N-alkylated protected amine described by structure (3a) where X is a chloride or bromide atom.

For example, the protected secondary amine (2) is dissolved in a suitable solvent, such as tetrahydrofuran and treated with one equivalent of a suitable base, such as sodium hydride. The reaction is allowed to stir for approximately 30 minutes and one equivalent of the appropriately substituted ethyl halocarboxylate, such as ethyl 4-bromobutyrate is added. The reaction is then heated to about 30° C. to 67° C. for about 1 to 24 hours. The N-alkylated protected amine (3a) is then isolated from the reaction medium by techniques well known in the art.

In step E the ester functionality of the N-alkylated protected amine (3a) is hydrolyzed under conditions well known in the art to provide the carboxylic acid (4).

For example, the N-alkylated protected amine (3a) is dissolved in a suitable solvent mixture, such as methanol/water and treated with an equivalent of a suitable base, such as sodium hydroxide. The reaction is allowed to stir at room temperature for about 1 to 24 hours. The reaction is then neutralized with 1N hydrochloric acid and the extracted with a suitable solvent, such as methylene chloride. The combined organic extracts are dried over anhydrous sodium sulfate, filtered and concentrated under vacuum to provide carboxylic acid (4).

The compounds of the formula (I) wherein $B_1$ and $B_4$ is H, and $B_2$ and $B_3$ is $-CH_2CH_2SH$ or $CH_2CH_2SPO_3H_2$ can be prepared as described in Scheme II. All substituents, unless otherwise indicated, are as previously defined. The reagents and starting materials are readily available to one of ordinary skill in the art.

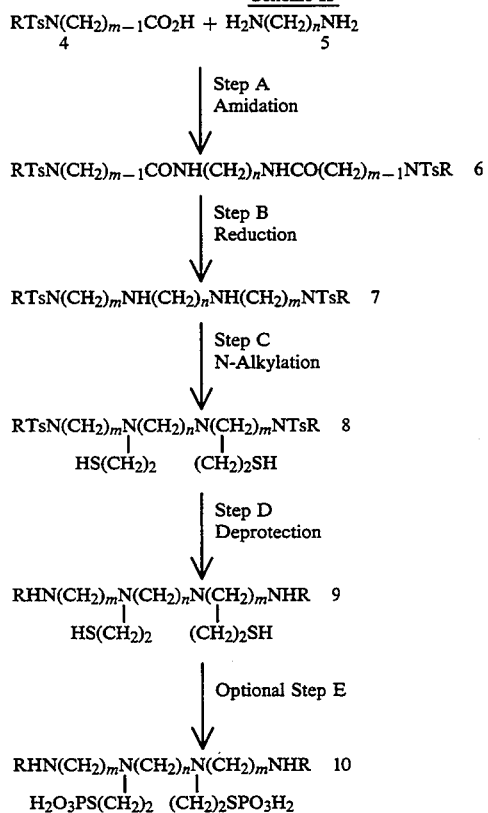

In Scheme II, step A, the diamine (5) is subjected to an amidation reaction under conditions well known in the art with 2 equivalents of the acid (4) to provide the diamide (6).

For example, 2 equivalents of the acid (4) is dissolved in a suitable organic solvent, such as tetrahydrofuran followed by addition of 1 equivalent of the appropriate diamine. Then 2.2 equivalents of N-ethoxycarbonyl-2- ethoxy-1,2-dihydroquinoline (EEDQ) is added. The reaction is stirred for 2 to 24 hours at room temperature. It is then concentrated under vacuum. The residue is purified by techniques well known in the art, such as flash chromatography to provide the diamide (6).

Alternatively the diamide (6) can be prepared in the manner described below. 2 equivalents of the acid (4) is dissolved in a suitable organic solvent, such as tetrahydrofuran and treated with 2 equivalents of N-methylmorpholine. The reaction is cooled to −20° C. and treated with 2 equivalents of isobutylchloroformate. The reaction is stirred for approximately 30 minutes and one equivalent of the appropriately substituted diamine (5) dissolved in dimethylformamide is added. The reaction is stirred at −20° C. for several hours, warmed to room temperature and diluted with ether and water. The layers are separated and the organic layer is dried over magnesium sulfate, filtered and concentrated under vacuum. The residue is purified by techniques well known in the art, such as flash chromatography to provide the diamide (6).

In step B the diamide (6) is reduced under conditions well known in the art to provide the tetra amine described by structure (7).

For example, following generally the procedure of Borch, *Tetrahedron Lett.* 1, 61 (1968), 2.2 equivalent of triethyloxonium tetrafluoroborate is dissolved in a suitable organic solvent, such as methylene chloride and 2 equivalents of the diamide (6) is added. The reaction is stirred at room temperature for approximately 24 hours and then the solvent is removed under vacuum. The residue is dissolved in ethanol and 4.5 equivalents of sodium borohydride is added in portions to the stirred solution at 0° C. After addition is completed, the reaction is warmed to room temperature and stirred for about 18 to 24 hours. The product is isolated by extractive techniques well known in the art. The residue can be purified by flash chromatography to provide the tetra amine (7).

Alternatively, the tetra amine (7) can be prepared in the manner described below. The diamide (6) is dissolved in a suitable solvent, such as tetrahydrofuran and treated with 2 equivalents of borane (1M solution in tetrahydrofuran) at 0° C. and stirred at reflux for 18 hours to provide the tetra amine (7) after isolation and purification by techniques that are well known in the art.

In step C, the tetra amine is di-N-alkylated with ethylene sulfide to provide the appropriately substituted di-N-alkylated amine described by structure (8).

For example the tetra amine (7) is dissolved in a suitable organic solvent, such as tetrahydrofuran and then treated with approximately 2.2 equivalents of ethylene sulfide for 2 to 10 hours at a temperature of from room temperature to reflux. The solvent is removed under vacuum and the product is isolated and purified by techniques well known in the art to provide the di-N-alkylated amine (8).

In step D, the di-N-alkylated amine (8) is deprotected by techniques well known in the art to provide the deprotected tetra amine (9).

For example the di-N-alkylated amine (8) dissolved in a suitable organic solvent such as 1,2-dimethoxyethane and treated with a slight excess of lithium aluminum hydride. The reaction is then heated to reflux for about 18 hours. After cooling the excess lithium aluminum hydride is quenched and the product is isolated following techniques well known in the art to provide the deprotected tetra amine (9).

Alternatively, the di-N-alkylated amine (8) can be deprotected following generally the procedure described in European Patent Application No. 349 224, published Mar. 1, 1990. The di-N-alkylated amine (8) is dissolved in dry tetrahydrofuran, cooled to −78° C. and treated with excess condensed ammonia. Excess sodium is added slowly at −78° C. and the reaction is stirred for approximately 4 hours. It is then warmed to room temperature overnight with evaporation of the ammonia. Diethyl ether is added followed by the cautious addition of ethanol followed by cautious addition of water to finally quench the reaction. The solvents are removed under vacuum and the residue extracted with diethyl ether and chloroform. The combined extracts are dried over anhydrous sodium sulfate, filtered and concentrated under vacuum. The residue is purified by techniques well known in the art such as flash chromatography to provide the deprotected amine (9).

In optional step E, the thiol functionalities of (9) may be converted to the corresponding phosphorothioates of structure (10).

For example, the appropriately substituted deprotected amine (9) is treated with 4 equivalents of triethyl phosphite and 2 equivalents of bromotrichloromethane. The reaction is stirred for from one to three hours at a temperature range of from room temperature to reflux. The corresponding intermediate bis(diethylphosphorothioate) is recovered from the reaction by removal of the volatiles under vacuum and purification by flash chromatography. The intermediate bis(diethylphosphorothioate) is then cleaved by treatment with excess trimethylsilyl bromide. The reactants are contacted in a suitable organic solvent such as methylene chloride for about 2 to 24 hours at a temperature range of from −20° C. to reflux. The volatiles are then removed under vacuum and the residue purified by techniques well known in the art to provide the phosphorothioates of structure (10).

The compounds of the formula (I) wherein $B_1$, $B_3$ and $B_4$ is H and $B_2$ is —$CH_2CH_2SH$ or $CH_2CH_2SPO_3H_2$, can be prepared as described in Scheme III. All substituents, unless otherwise indicated, are previously defined. The reagents and starting materials are readily available to one of ordinary skill in the art.

Scheme III $RTsN(CH_2)_{m-1}CONH(CH_2)_nNHCO(CH_2)_{m-1}NTsR$  6

Step A
Reduction $RTsN(CH_2)_mNH(CH_2)_nNHCO(CH_2)_{m-1}NTsR$  11

Step B
N-Alkylation $RTsN(CH_2)_mN(CH_2)_nNHCO(CH_2)_{m-1}NTsR$  12
|
$HS(CH_2)_2$ Step C
Deprotection/
Reduction -continued

Scheme III

RTN(CH$_2$)$_m$N(CH$_2$)$_n$NH(CH$_2$)$_m$NHR    13
|
HS(CH$_2$)$_2$

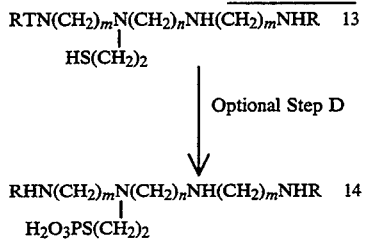

Optional Step D

RHN(CH$_2$)$_m$N(CH$_2$)$_n$NH(CH$_2$)$_m$NHR    14
|
H$_2$O$_3$PS(CH$_2$)$_2$

In Scheme III, step A the diamide (6) prepared in Scheme II, step A is reduced utilizing one equivalent of a suitable reducing agent under conditions well known in the art to provide the mono-amide described by structure (11).

For example, the diamide (6) is dissolved in a suitable organic solvent, such as tetrahydrofuran and treated with 1 equivalent of borane (1M solution in tetrahydrofuran) at 0° C. and then stirred for 6 to 8 hours at reflux to provide the mono-amide (11) after isolation and purification by techniques that are well known in the art.

In step B the mono-amide is mono-N-alkylated with ethylene sulfide to provide the appropriately substituted mono-N-alkylated amide described by structure (12).

For example, the mono-amide (11) is dissolved in a suitable organic solvent, such as benzene and then treated with 1 equivalent of ethylene sulfide for 2 to 10 hours at a temperature of from room temperature to reflux. The solvent is removed under vacuum and the product isolated and purified by techniques well known in the art to provide the mono-N-alkylated amide (12).

In step C, the mono-N-alkylated amide (12) is deprotected and concomitantly reduced by treatment with a suitable reducing agent to provide the mono-N-alkylated tetra amine described by structure (13).

For example, the mono-N-alkylated amide (12) is dissolved in a suitable organic solvent, such as 1,2-dimethoxyethane and treated with 4 equivalents of a suitable reducing agent, such as lithium aluminum hydride. The reaction is heated to reflux for about 18 hours. The reaction is then quenched by addition of water:10% sodium hydroxide:water in the ratio of 1.0:1.5:3.0 by volume where the first addition of water is equivalent to the amount of lithium aluminum hydride used by weight. The product is then isolated by extractive and purification techniques that are well known in the art to provide the mono-N-alkylated tetra amine (13).

In optional step D, the thiol functionality of the mono-N-alkylated tetra amine (13) can be converted to the corresponding mono-phosphorothioate of structure (14) following generally the procedure described in Scheme II, optional step E.

For example, the appropriately substituted mono alkylated tetra amine (13) is treated with 2 equivalents of triethyl phosphite and 1 equivalent of bromotrichloromethane. The reaction is stirred for from one to three hours at a temperature range of from room temperature to reflux. The corresponding intermediate diethylphosphorothioate is recovered from the reaction by removal of the volatiles under vacuum and purification by flash chromatography. The intermediate diethylphosphorothioate is then cleaved by treatment with excess trimethylsilyl bromide. The reactants are contacted in a suitable organic solvent such as methylene chloride for about 2 to 24 hours at a temperature range of from −20° C. to reflux. The volatiles are then removed under vacuum and the residue purified by techniques well known in the art to provide the mono-phosphorothioate of structure (14).

The compounds of formula (I) wherein B$_1$ and B$_4$ is —CH$_2$CH$_2$SH or CH$_2$CH$_2$SPO$_3$H$_2$ and B2 and B3 is H can be prepared as described in Scheme IV. All substituents, unless otherwise indicated, are previously defined. The reagents and starting materials are readily available to one of ordinary skill in the art.

Scheme IV

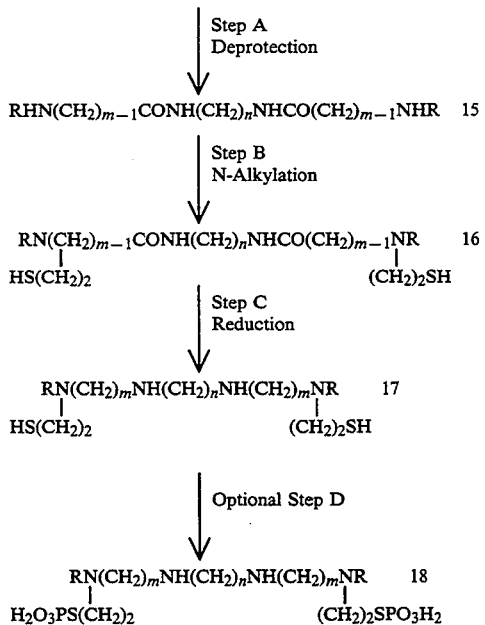

In Scheme IV, step A the diamide (6) prepared in Scheme II, step A is deprotected under conditions well known in the art to provide the deprotected diamide described by structure (15).

For example, the diamide (6) can be deprotected following generally the procedure described in European Patent Application No. 349 224, published Mar. 1, 1990. The diamide (6) is dissolved in dry tetrahydrofuran, cooled to −78° C. and treated with excess condensed ammonia. Excess sodium is added slowly at −78° C. and the reaction is stirred for approximately 4 hours. It is then warmed to room temperature overnight with evaporation of the ammonia. Diethyl ether is added followed by the cautious addition of ethanol followed by cautious addition of water to finally quench the reaction. The solvents are removed under vacuum and the residue extracted with diethyl ether and chloroform. The combined extracts are dried over anhydrous sodium sulfate, filtered and concentrated under vacuum. The residue is purified by techniques well known in the art such as flash chromatography to provide the deprotected diamide (15).

In step B the deprotected diamide (15) is di-N-alkylated in a manner analogous to the N-alkylation procedure previously described in Scheme II, step C to provide the di-N-alkylated diamide described by structure (16).

In step C the di-N-alkylated diamide (16) is reduced under conditions well known in the art to provide the tetra amine described by structure (17).

For example, the di-N-alkylated diamide (16) is dissolved in a suitable organic solvent, such as 1,2-dimethoxyethane and treated with 2 equivalents of a suitable reducing agent, such as lithium aluminum hydride. The reaction is heated to reflux for about 5 to 18 hours. The reaction is then quenched by addition of water:10% sodium hydroxide:water in the ratio of 1.0:1.5:3.0 by volume where the first addition of water is equivalent to the amount of lithium aluminum hydride used by weight. The product is then isolated by extractive and purification techniques that are well known in the art to provide the tetra amine (17).

In optional step D the thiol functionalities of tetra amine (17) may be converted to the corresponding phosphorothioates of structure (18) in a manner analogous to the procedure previously described in Scheme II, optional step E.

The compounds of formula (I) wherein $B_1$, $B_2$ and $B_3$ is H and $B_4$ is $-CH_2CH_2SH$ or $CH_2CH_2SPO_3H_2$, can be prepared as described in Scheme V. All substituents, unless otherwise indicated, are previously defined. The reagents and starting materials are readily available to one of ordinary skill in the art.

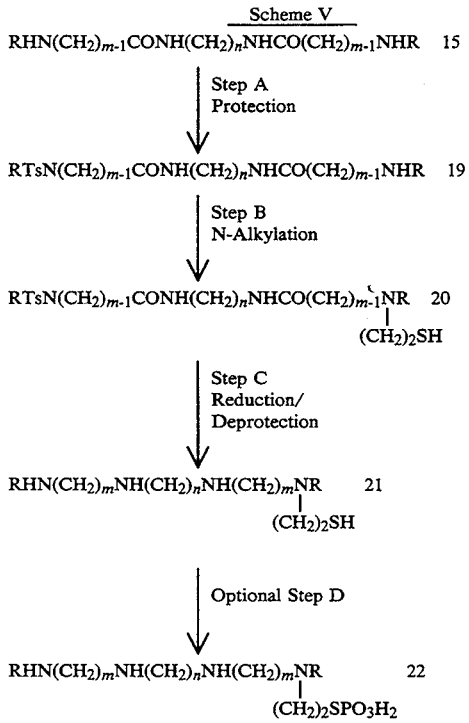

In Scheme V, step A the deprotected diamide (15) prepared in Scheme IV, step A is mono-protected to provide the mono-protected diamide described by structure (19).

For example the deprotected diamide (15) is dissolved in methylene chloride and 10% sodium hydroxide and cooled to 0° C. To the stirring solution is added dropwise one equivalent of p-toluenesulfonyl chloride. After approximately 1 hour the reaction is warmed to room temperature and allowed to stir for 1 to 48 hours. The reaction is neutralized with 0.5N hydrochloric acid and extracted with a suitable organic solvent, such as methylene chloride. The organic phase is rinsed with water, brine, dried over anhydrous sodium sulfate, filtered and concentrated under vacuum to provide the mono-protected diamide (19).

In step B the mono-protected diamide (19) is N-alkylated in a manner analogous to the N-alkylation previously described in Scheme III, step B to provide the N-alkylated diamide described by structure (20).

In step C the N-alkylated diamide (20) is reduced and concomitantly deprotected in a manner analogous to the procedure previously described in Scheme III, step C to provide the N-alkylated tetra amine described by structure (21).

In optional step D the thiol functionality of the N-alkylated tetra amine (21) can be converted to the corresponding phosphorothioate tetra amine described by structure (22) following generally the procedure described in Scheme III, optional step D.

The following examples represent typical syntheses of the compounds of formula (I) as described by Schemes I, II, III, IV and V. These examples are illustrative only and are not intended to limit the invention in any way. The reagents and starting materials are readily available to one of ordinary skill in the art. As used in the following examples, the following terms have the meanings indicated: "eq." refers to equivalents, "g" refers to grams, "mg" refers to milligrams, "mmol" refers to millimoles, "mL" refers to milliliters, "°C." refers to degrees Celsius, "TLC" refers to thin layer chromatography, "$R_f$" refers to retention factor and "$\delta$" refers to parts per million down field from tetramethylsilane.

EXAMPLE 1

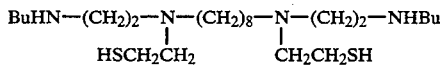

Preparation of 2-[{8-[(2-Mercapto-ethyl)-(2-butylamino-ethyl)-amino]-octyl}-(2-butylamino-ethyl-amino]-ethanethiol.

Scheme I, step A; Dissolve butylamine (10 mmol) in methylene chloride (50 mL) and 10% sodium hydroxide (50 mL). Cool to 0° C. Add excess p-toluenesulfonyl chloride with stirring. After 1 hour allow the reaction to warm to room temperature and stir for 2 days. Neutralize the reaction with 0.5N hydrochloric acid and extract the aqueous with methylene chloride (2×100 mL). Rinse the combined organic extracts with water (100 mL), brine (100 mL), dry over anhydrous sodium sulfate, filter and concentrate under vacuum to provide N-butyl-4-methyl-benzenesulfonamide.

Scheme I, step B; Dissolve N-butyl-4-methyl-benzenesulfonamide (10 mmol) in tetrahydrofuran (50 mL) and add triphenylphosphine (10 mmol). Treat this with ethylene glycol (10 mmol) followed by addition of diethyl azodicarboxylate (10 mmol). Stir the reaction at 25° C. for 18 hours. Concentrate the reaction under vacuum. Purify the residue by flash chromatography (silica gel, toluene/ethyl acetate) to provide N-butyl-N-(2-hydroxy-ethyl)-4-methyl-benzenesulfonamide.

Scheme I, step C; Dissolve N-butyl-N-(2-hydroxyethyl)-4-methyl-benzenesulfonamide (10 mmol) in acetone (50 mL) and cool to 0° C. Add a slight excess of Jones reagent dropwise and allow the reaction to stir for 4 hours at 0° C. Add excess isopropanol and filter the reaction through a plug of diatomaceous earth. Rinse the plug with acetone (2×50 mL) and methylene chloride (3×50 mL). Combine the filtrates and concentrate under vacuum. Purify the residue by flash chromatography (silica gel, methanol/methylene chloride) to provide [butyl-(toluene-4-sulfonyl)-amino]-acetic acid.

Alternative method of preparation of [butyl-(toluene-4-sulfonyl)-amino]-acetic acid.

Scheme I, step D; Dissolve N-butyl-4-methyl-benzenesulfonamide (10 mmol) in tetrahydrofuran (50 mL) and treat with sodium hydride (10 mmol). Stir the reaction for 30 minutes and add ethyl bromoacetate (10 mmol). Stir the reaction at reflux for 18 hours. Then add methylene chloride (100 mL) and rinse with water (100 mL), brine (100 mL), dry over anhydrous sodium sulfate, filter and concentrate to provide crude ethyl-[butyl-(toluene-4-sulfonyl)-amino]-acetate.

Scheme I, step E; Dissolve the crude ethyl-[butyl-(toluene-4-sulfonyl)-amino]-acetate (10 mmol) in methanol (25 mL) and water (25 mL). Add sodium hydroxide (10 mmol) and stir the reaction at room temperature for 5 hours. Dilute the reaction with water (100 mL) and rinse with methylene chloride. Neutralize the aqueous with 1N hydrochloric acid and extract with methylene chloride (3×75 mL). Combine the organic extracts and rinse with water (100 mL), brine (100 mL), dry over anhydrous sodium sulfate, filter and concentrate under vacuum to provide [butyl-(toluene-4-sulfonyl)-amino]-acetic acid.

Scheme II, step A; Dissolve [butyl-(toluene-4-sulfonyl)-amino]-acetic acid (20 mmol) prepared in Scheme I step C or step E in tetrahydrofuran (50 mL) and add 1,8-diaminooctane (10 mmol). Add N-ethoxycarbonyl-2-ethoxy-1,2-dihydroquinoline (EEDQ) (22 mmol). Stir at room temperature for 6 to 7 hours. Concentrate the reaction under vacuum. Purify the residue by flash chromatography (silica gel, methanol/methylene chloride) to provide the diamide.

Alternatively the diamide can be prepared in Scheme II, step A by dissolving [butyl-(toluene-4-sulfonyl)-amino]-acetic acid (20 mmol) in tetrahydrofuran (50 mL) followed by addition of N-methylmorpholine (20 mmol). Cool the reaction to −20° C. and add isobutyl chloroformate (20 mmol). Stir the reaction for 30 minutes and add 1,8-diaminooctane (10 mmol) dissolved in dimethylformamide (5 mL). Stir the reaction for 2 hours at −20° C. and then warm to room temperature. Dilute the reaction with water (150 mL) and extract with diethyl ether (3×75 ml). Combine the organic extracts, dry over anhydrous magnesium sulfate, filter and concentrate under vacuum. Purify the residue by flash chromatography (silica gel, methanol/methylene chloride) to provide the diamide.

Scheme II, step B; Add triethyloxonium tetrafluoroborate (42 mmol) in methylene chloride (50 mL) and add the diamide (20 mmol) prepared above in Scheme II, step A. Stir the reaction at room temperature for 24 hours and then concentrate under vacuum. Dissolve the residue in ethanol (50 mL), cool to 0° C. and add sodium borohydride (45 mmol) portionwise. After complete addition warm the reaction to room temperature and stir for 24 hours. Dilute the reaction with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the tetra amine.

Alternatively the tetra amine can be prepared in Scheme II, step B by dissolving the diamide (10 mmol) prepared in Scheme II, step A in tetrahydrofuran (50 mL). Cool the solution to 0° C. and add borane (20 mmol, 1M solution in tetrahydrofuran. Heat the reaction to reflux for 18 hours. After cooling, dilute the reaction with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the tetra amine.

Scheme II, step C; Dissolve the tetra amine (10 mmol) prepared in Scheme II, step B in tetrahydrofuran (50 mL) and add dropwise ethylene sulfide (22 mmol). Heat the reaction to reflux for 4 hours. After cooling, concentrate the reaction under vacuum and purify the residue by flash chromatography (silica gel, methanol/methylene chloride) to provide the di-N-alkylated tetra amine.

Scheme II, step D; Dissolve the di-N-alkylated tetra amine (10 mmol) prepared in Scheme II, step C in 1,2-dimethoxyethane (50 mL) and treat with lithium aluminum hydride (25 mmol). Heat the reaction to reflux for 18 hours. After cooling the reaction is worked up by consecutive addition of water (1 mL), 10% sodium hydroxide (1.5 mL) and water (3 mL). Then dilute with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the title compound.

Alternatively the title compound can be prepared in Scheme II, step D by dissolving the di-N-alkylated tetra amine (10 mmol) prepared in Scheme II, step C in dry tetrahydrofuran (50 mL) and cooling the solution to −78° C. Add excess dry ammonia followed by excess sodium. Stir the reaction for 4 hours and then warm to room temperature overnight. Add diethyl ether (100 mL) followed by cautious addition of ethanol (30 mL). After stirring for 30 minutes cautiously add water dropwise (5 mL) and then concentrate the reaction under vacuum. Extract the residue with diethyl ether (100 mL) and chloroform (100 mL). Combine the organic extracts, dry over anhydrous sodium sulfate, filter and concentrate under vacuum. Purify the residue by flash chromatography (silica gel, methanol/methylene chloride) to provide the title compound.

EXAMPLE 2

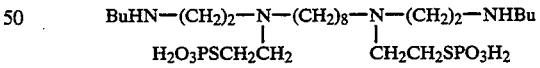

Preparation of 5,8,17,20-tetraaza-8,17-bis-[2-(thiophosphoryl)ethyl]-tetradodecane.

Scheme II, optional step E; Treat 2-((2-Butylamino-ethyl)-{8-[(2-butylamino-ethyl)-(2-mercapto-ethyl)-amino]-octyl}-amino)-ethanethiol (10 mmol) prepared in example 1, with triethyl phosphite (40 mmol) and bromotrichloromethane (20 mmol). Stir the reaction for 2 hours at reflux. Concentrate the reaction under vacuum and purify the the intermediate bis(diethylphosphorothioate) by flash chromatography (silica gel, ethyl acetate). The purified bis(diethylphosphorothioate) is then dissolved in methylene chloride (50 mL) and treated with excess trimethylsilyl bromide. Stir the reaction for 24 hours. Concentrate the reaction under vacuum to provide the title compound.

EXAMPLE 3

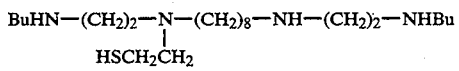

Preparation of 2-{(2-Butylamino-ethyl)-[8-(2-butylamino-ethylamino)-actyl]amino}-ethanethiol.

Scheme III, step A; Dissolve triethyloxonium tetrafluoroborate (10 mmol) in methylene chloride (50 mL) and add the diamide (10 mmol) prepared in example 1, Scheme II, step A. Stir the reaction at room temperature for 24 hours and then concentrate under vacuum. Dissolve the residue in ethanol (50 mL), cool to 0° C. and add sodium borohydride (45 mmol) portionwise. After complete addition warm the reaction to room temperature and stir for 24 hours. Dilute the reaction with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the amide.

Alternatively the amide can be prepared in Scheme III, step A by dissolving the diamide (10 mmol) prepared in example 1, Scheme II, step A in tetrahydrofuran (50 mL). Cool the solution to 0° C. and add borane (10 mmol, 1M solution in tetrahydrofuran. Heat the reaction to reflux for 18 hours. After cooling, dilute the reaction with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the amide.

Scheme III, step B; Dissolve the amide (10 mmol) prepared in Scheme III, step A in tetrahydrofuran (50 mL) and add dropwise ethylene sulfide (10 mmol). Heat the reaction to reflux for 4 hours. After cooling, concentrate the reaction under vacuum and purify the residue by flash chromatography (silica gel, methanol/methylene chloride) to provide the N-alkylated amide.

Scheme III, step C; Dissolve the N-alkylated amide (10 mmol) prepared in Scheme III, step B in 1,2-dimethoxyethane (50 mL) and treat with lithium aluminum hydride (40 mmol). Heat the reaction to reflux for 18 hours. After cooling the reaction is worked up by consecutive addition of water (1.5 mL), 10% sodium hydroxide (2.3 mL) and water (4.5 mL). Then dilute with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the title compound.

EXAMPLE 4

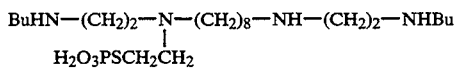

Preparation of 5,8,17,20-tetraaza-8-[2(thiophosphoryl-)ethyl]-tetradodecane.

Scheme III, optional step D; Treat 2-{(2-Butylamino-ethyl)-[8-(2-butylamino-ethylamino)-octyl]-amino}-ethanethiol (10 mmol) prepared in example 3, with triethyl phosphite (20 mmol) and bromotrichloromethane (10 mmol). Stir the reaction for 2 hours at reflux. Concentrate the reaction under vacuum and purify the the intermediate diethylphosphorothioate by flash chromatography (silica gel, ethyl acetate). The purified diethylphosphorothioate is then dissolved in methylene chloride (50 mL) and treated with excess trimethylsilyl bromide. Stir the reaction for 4 hours at −20° C. Concentrate the reaction under vacuum. Dissolve the residue in 2-propanol, add hydrochloric acid and collect the title compound by filtration as the hydrochloride salt.

EXAMPLE 5

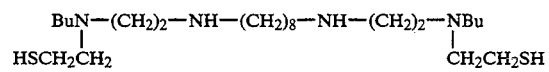

Preparation of 2-{Butyl-[2-(8-{2-[butyl-(2-mercapto-ethyl)-amino]-ethylamino}-octylamino))-ethyl]-amino}-ethanethiol.

Scheme IV, step A; Dissolve the diamide (10 mmol) prepared in example 1, Scheme II, step A in dry tetrahydrofuran (50 mL) and cool the solution to −78° C. Add excess dry ammonia followed by excess sodium. Stir the reaction for 4 hours and then warm to room temperature overnight. Add diethyl ether (100 mL) followed by cautious addition of ethanol (30 mL). After stirring for 30 minutes cautiously add water dropwise (5 mL) and then concentrate the reaction under vacuum. Extract the residue with diethyl ether (100 mL) and chloroform (100 mL). Combine the organic extracts, dry over anhydrous sodium sulfate, filter and concentrate under vacuum. Purify the residue by flash chromatography (silica gel, methanol/methylene chloride) to provide the deprotected diamide.

Scheme IV, step B; Dissolve the deprotected diamide (10 mmol) prepared in Scheme IV, step A in tetrahydrofuran (50 mL) and add dropwise ethylene sulfide (22 mmol). Heat the reaction to reflux for 4 hours. After cooling, concentrate the reaction under vacuum and purify the residue by flash chromatography (silica gel, methanol/methylene chloride) to provide the di-N-alkylated diamide.

Scheme IV, step C; Dissolve the di-N-alkylated diamide (10 mmol) prepared in Scheme IV, step B in 1,2-dimethoxyethane (50 mL) and treat with lithium aluminum hydride (40 mmol). Heat the reaction to reflux for 18 hours. After cooling the reaction is worked up by consecutive addition of water (1.5 mL), 10% sodium hydroxide (2.3 mL) and water (4.5 mL). Then dilute with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the title compound.

EXAMPLE 6

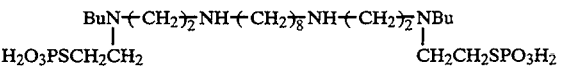

Preparation of 5,8,17,20-tetraaza-5,20-bis[2-(thiophsophoryl)ethyl]-tetradodecane.

Scheme IV, optional step D; Treat 2-{Butyl-[2-(8-{2-[butyl-(2-mercapto-ethyl)-amino]-ethylamino}-octylamino))-ethyl]-amino}-ethanethiol (10 mmol) prepared in example 5 with triethyl phosphite (40 mmol)

and bromotrichloromethane (20 mmol). Stir the reaction for 2 hours at reflux°C. Concentrate the reaction under vacuum and purify the the intermediate bis(diethylphosphorothioate) by flash chromatography (silica gel, ethyl acetate). The purified bis(diethylphosphorothioate) is then dissolved in methylene chloride (50 mL) and treated with excess trimethylsilyl bromide. Stir the reaction for 4 hours at −20° C. Concentrate the reaction under vacuum. Dissolve the residue in 2-propanol, add hydrochloric acid and collect the title compound by filtration as the hydrochloride salt.

EXAMPLE 7

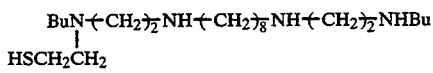

Preparation of 2-(Butyl-{2-[8-(2-butylamino-ethylamino)-octylamino]-ethyl}-amino)-ethanethiol.

Scheme V, step A; Dissolve the deprotected diamide (10 mmol) prepared in example 5, Scheme IV, step A in 10% sodium hydroxide (50 mL) and cool to 0° C. Add p-toluenesulfonyl chloride (10 mmol) with stirring. After 1 hour allow the reaction to warm to room temperature and stir for 2 days. Neutralize the reaction with 0.5N hydrochloric acid and extract the aqueous with methylene chloride (2×100 mL). Rinse the combined organic extracts with water (100 mL), brine (100 mL), dry over anhydrous sodium sulfate, filter and concentrate under vacuum to provide the mono-protected diamide.

Scheme V, step B; Dissolve the mono-protected diamide (10 mmol) prepared in Scheme V, step A in tetrahydrofuran (50 mL) and add dropwise ethylene sulfide (1.2 mmol). Heat the reaction to reflux for 4 hours. After cooling, concentrate the reaction under vacuum and purify the residue by flash chromatography (silica gel, methanol/methylene chloride) to provide the N-alkylated diamide.

Scheme V, step C; Dissolve the N-alkylated diamide (10 mmol) prepared in Scheme V, step B in 1,2-dimethoxyethane (50 mL) and treat with lithium aluminum hydride (40 mmol). Heat the reaction to reflux for 18 hours. After cooling the reaction is worked up by consecutive addition of water (1.5 mL), 10% sodium hydroxide (2.3 mL) and water (4.5 mL). Then dilute with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the title compound.

EXAMPLE 8

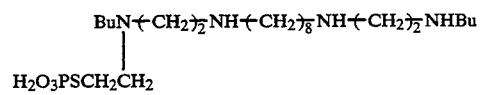

Preparation of 5,8,17,20-tetraaza-5-[2(thiophosphoryl)ethyl]-tetradodecane.

Scheme V, optional step D; Treat 2-(Butyl-{2-[8-(2-butylamino-ethylamino)-octylamino]-ethyl}-amino)-ethanethiol (10 mmol) prepared in example 7 with triethyl phosphite (20 mmol) and bromotrichloromethane (10 mmol). Stir the reaction for 2 hours at reflux. Concentrate the reaction under vacuum and purify the the intermediate diethylphosphorothioate by flash chromatography (silica gel, ethyl acetate). The purified diethylphosphorothioate is then dissolved in methylene chloride (50 mL) and treated with excess trimethylsilyl bromide. Stir the reaction for 4 hours at −20° C. Concentrate the reaction under vacuum. Dissolve the residue in 2-propanol, add hydrochloric acid and collect the title compound by filtration as the hydrochloride salt.

The polyamine derivatives of formula (II) can be prepared utilizing techniques well known in the art. The choice of any specific route of preparation is dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (II).

The following reaction schemes are illustrative of the pathways by which the compounds of formula (II) may be made. All substituents, unless otherwise indicated, are previously defined. The reagents and starting materials are readily available to one of ordinary skill in the art. Preparation of starting material for use in Schemes VII, VIII and IX is described in Scheme VI.

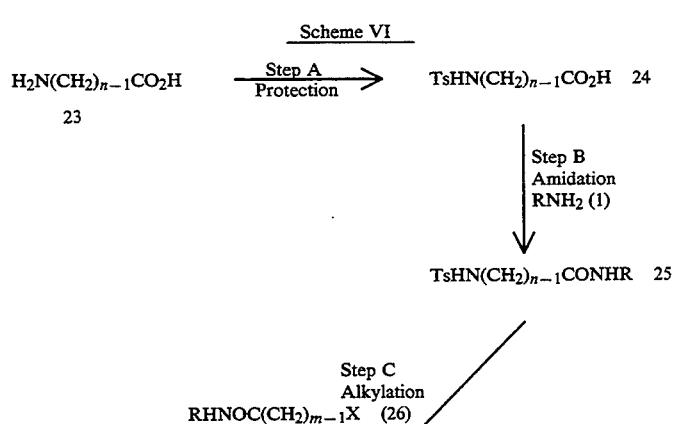

Scheme VI

RHNOC(CH$_2$)$_{m-1}$NTs(CH$_2$)$_{n-1}$CONHR  27

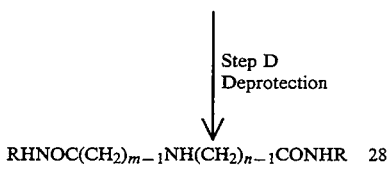

Step D
Deprotection

RHNOC(CH$_2$)$_{m-1}$NH(CH$_2$)$_{n-1}$CONHR  28

In Scheme VI, step A the amino acid described by structure (23) is protected to provide the N-tosylated amino acid described by structure (24). For example the amino acid (23) is dissolved in 10% sodium hydroxide and cooled to 0° C. To the stirring solution is added dropwise an equivalent of p-toluenesulfonyl chloride. After approximately 1 hour the reaction is warmed to room temperature and allowed to stir for abut 2 days. The reaction is neutralized with 0.5N hydrochloric acid and extracted with a suitable organic solvent, such as methylene chloride. The organic phase is rinsed with water, brine, dried over anhydrous sodium sulfate, filtered and concentrated under vacuum to provide the N-tosylated amino acid (24).

In step B the N-tosylated amino acid (24) is subjected to an amidation reaction under conditions well known in the art with an appropriately substituted primary amine (1) to provide the amide described by structure (25).

For example, the N-tosylated amino acid (24) is dissolved in a suitable organic solvent, such as tetrahydrofuran followed by addition of 1 equivalent of the appropriately substituted primary amine (1). Then 1.1 equivalents of N-ethoxycarbonyl-2-ethoxy-1,2-dihydroquinoline (EEDQ) is added and the reaction is stirred for 2 to 24 hours at room temperature. The reaction is then concentrated under vacuum. The residue is purified by techniques well known in the art, such as flash chromatography to provide the amide (25).

Alternatively the amide (25) can be prepared in the manner described below. 1 equivalent of the N-tosylated amino acid (24) is dissolved in a suitable organic solvent, such as tetrahydrofuran and treated with 1 equivalent of N-methylmorpholine. The reaction is cooled to −20° C. and treated with 1 equivalent of isobutylchloroformate. The reaction is stirred for approximately 30 minutes and one equivalent of the appropriately substituted primary amine (1) dissolved in dimethylformamide is added. The reaction is stirred at −20° C. for several hours, warmed to room temperature and diluted with ether and water. The layers are separated and the organic layer is dried over magnesium sulfate, filtered and concentrated under vacuum. The residue is purified by techniques well known in the art, such as flash chromatography to provide the amide (25).

In step C the amide (25) is N-alkylated with the appropriately substituted halo-amide of structure (26) to provide the protected diamide described by structure (27).

For example, the amide (25) is dissolved in a suitable solvent, such as tetrahydrofuran and treated with one equivalent of a suitable base, such as sodium hydride. The reaction is allowed to stir for approximately 30 minutes and one equivalent of the appropriately substituted halo-amide (26) is added [The halo-amide (26) can be prepared under conditions well known in the art such as an amidation reaction between X(CH$_2$)$_{m-1}$COX and RNH$_2$ [1] where X is a chloride or bromide atom]. The reaction is then heated to about 30° C. to 67° C. for about 1 to 24 hours. The protected diamide (27) is then isolated from the reaction medium by techniques well known in the art. For example the reaction is diluted with methylene chloride, rinsed with water, brine, dried over anhydrous sodium sulfate, filtered and concentrated under vacuum. The residue is purified by techniques well known in the art, such as flash chromatography on silica gel with a suitable eluent mixture, such as methanol/methylene chloride to provide the protected diamide (27).

In step H, the protected diamide (27) is deprotected under conditions well known in the art to provide the deprotected diamide described by structure (28).

For example the protected diamide (27) can be deprotected following generally the procedure described in European Patent Application No. 349 224, published Mar. 1, 1990. The protected diamide (27) is dissolved in dry tetrahydrofuran, cooled to −78° C. and treated with excess condensed ammonia. Excess sodium is added slowly at −78° C. and the reaction is stirred for approximately 4 hours. It is then warmed to room temperature overnight with evaporation of the ammonia. Diethyl ether is added followed by the cautious addition of ethanol followed by cautious addition of water to finally quench the reaction. The solvents are removed under vacuum and the residue extracted with diethyl ether and chloroform. The combined extracts are dried over anhydrous sodium sulfate, filtered and concentrated under vacuum. The residue is purified by techniques well known in the art such as flash chromatography to provide the deprotected diamide (28).

The compounds of formula (II) wherein B$_2$ and B$_3$ is H, and B$_1$ is —CH$_2$CH$_2$SH or —CH$_2$CH$_2$SPO$_3$H$_2$, can be prepared as described in Scheme VII. All substituents, unless otherwise indicated, are previously defined. The reagents and starting materials are readily available to one of ordinary skill in the art.

Scheme VII

RHNCO(CH$_2$)$_{m-1}$NTs(CH$_2$)$_{n-1}$CONHR  27

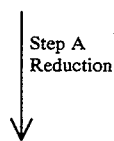

Step A
Reduction

Scheme VII

RHN(CH$_2$)$_m$NTs(CH$_2$)$_{n-1}$CONHR  29

Step B
N-Alkylation

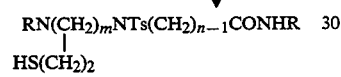
RN(CH$_2$)$_m$NTs(CH$_2$)$_{n-1}$CONHR  30
|
HS(CH$_2$)$_2$

Step C
Deprotection/
Reduction

RN(CH$_2$)$_m$NH(CH$_2$)$_n$NHR  31
|
HS(CH$_2$)$_2$

Optional Step D

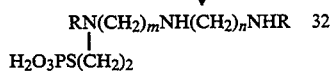
RN(CH$_2$)$_m$NH(CH$_2$)$_n$NHR  32
|
H$_2$O$_3$PS(CH$_2$)$_2$

In Scheme VII, step A the appropriately substituted diamide (27) prepared in Scheme VI, step C is reduced under conditions well known in the art to the mono-amide described by structure (29).

For example, the diamide (27) is dissolved in a suitable solvent, such as tetrahydrofuran and treated with equivalent of borane (1M solution in tetrahydrofuran) at 0° C. It is then stirred for 3 hours at reflux to provide the mono-amide (29) after isolation and purification by techniques that are well known in the art.

In step B the mono-amide (29) is mono-N-alkylated with ethylene sulfide to provide the appropriately substituted mono-N-alkylated amide described by structure (30).

For example, the mono-amide (29) is dissolved in a suitable organic solvent, such as benzene and then treated with 1 equivalent of ethylene sulfide for 2 to 10 hours at a temperature of from room temperature to reflux to provide the mono-N-alkylated amide (30).

In step C, the mono-N-alkylated amide (30) is deprotected and concomitantly reduced by treatment with a suitable reducing agent to provide the mono-N-alkylated triamine described by structure (31).

For example, the mono-N-alkylated amide (30) is dissolved in a suitable organic solvent, such as 1,2-dimethoxyethane and treated with 4 equivalents of a suitable reducing agent, such as lithium aluminum hydride. The reaction is heated to reflux for about 18 hours. The reaction is then quenched by addition of water:10% sodium hydroxide:water in the ratio of 1.0:1.5:3.0 by volume where the first addition of water is equivalent to the amount of lithium aluminum hydride used by weight. The product is then isolated by extractive and purification techniques that are well known in the art to provide the mono-N-alkylated triamine (31).

In optional step D, the thiol functionality of the mono-N-alkylated triamine (31) can be converted to the corresponding mono-phosphorothioate of structure (32), following generally the procedure described in Scheme III, optional step D.

For example, the appropriately substituted mono-N-alkylated triamine (31) is treated with 2 equivalents of triethyl phosphite and 1 equivalent of bromotrichloromethane. The reaction is stirred for from one to three hours at a temperature range of from room temperature to reflux. The corresponding intermediate diethylphosphorothioate is recovered from the reaction by removal of the volatiles under vacuum and purification by flash chromatography. The intermediate diethylphosphorothioate is then cleaved by treatment with excess trimethylsilyl bromide. The reactants are contacted in a suitable organic solvent such as methylene chloride for about 2 to 24 hours at a temperature range of from −20° C. to reflux. The volatiles are then removed under vacuum and the residue purified by techniques well known in the art to provide the mono-phosphorothioate of structure (32).

The compounds of the formula (II) wherein B$_1$ and B$_3$ is H and B$_2$ is —CH$_2$CH$_2$SH or CH$_2$CH$_2$SPO$_3$H$_2$ can be prepared as described in Scheme VIII. All substituents, unless otherwise indicated, are previously defined. The reagents and starting materials are readily available to one of ordinary skill in the art.

Scheme VIII

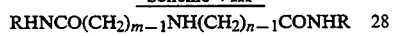
RHNCO(CH$_2$)$_{m-1}$NH(CH$_2$)$_{n-1}$CONHR  28

Step A
N-Alkylation

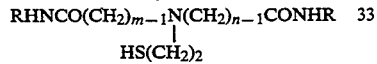
RHNCO(CH$_2$)$_{m-1}$N(CH$_2$)$_{n-1}$CONHR  33
|
HS(CH$_2$)$_2$

Step B
Reduction

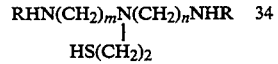
RHN(CH$_2$)$_m$N(CH$_2$)$_n$NHR  34
|
HS(CH$_2$)$_2$

Optional Step C

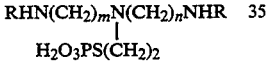
RHN(CH$_2$)$_m$N(CH$_2$)$_n$NHR  35
|
H$_2$O$_3$PS(CH$_2$)$_2$

In Scheme VIII, step A the appropriately substituted diamide (28) prepared in Scheme VI, step D is mono-N-alkylated with ethylene sulfide to provide the appropriately substituted mono-N-alkylated diamide described by structure (33).

For example, the appropriately substituted diamide (28) is dissolved in a suitable organic solvent, such as benzene and then treated with 1 equivalent of ethylene sulfide for 2 to 10 hours at a temperature of from room temperature to reflux to provide the mono-N-alkylated diamide (33).

In step B, the mono-N-alkylated diamide (33) is deprotected and concomitantly reduced by treatment with a suitable reducing agent to provide the mono-N-alkylated triamine described by structure (34).

For example, the mono-N-alkylated diamide (33) is dissolved in a suitable organic solvent, such as 1,2-dimethoxylethane and treated with 4 equivalents of a suitable reducing agent, such as lithium aluminum hydride. The reaction is heated to reflux for about 18 hours. The reaction is then quenched by addition of water:10% sodium hydroxide:water in the ratio of 1.0:1.5:3.0 by volume where the first addition of water is equivalent to the amount of lithium aluminum hydride used by weight. The product is then isolated by extractive and purification techniques that are well known in the art to provide the mono-N-alkylated triamine (34).

In optional step C, the thiol functionality of the mono-N-alkylated triamine (34) can be converted to the corresponding mono-phosphorothioate of structure (35) following generally the procedure described in Scheme V, optional step D.

For example, the appropriately substituted mono-N-alkylated triamine (34) is treated with 2 equivalents of triethyl phosphite and 1 equivalent of bromotrichloromethane. The reaction is stirred for from one to three hours at a temperature range of from $-20°$ C. to reflux. The corresponding intermediate diethylphosphorothioate is recovered from the reaction by removal of the volatiles under vacuum and purification by flash chromatography. The intermediate diethylphosphorothioate is then cleaved by treatment with excess trimethylsilyl bromide. The reactants are contacted in a suitable organic solvent such as methylene chloride for about 2 to 24 hours at a temperature range of from room temperature to reflux. The volatiles are then removed under vacuum and the residue purified by techniques well known in the art to provide the mono-phosphorothioate of structure (35).

The compounds of the formula (II) wherein $B_1$ and $B_3$ is $-CH_2CH_2SH$ or $CH_2CH_2SPO_3H_2$ and $B_2$ is H can be prepared as described in Scheme IX. All substituents, unless otherwise indicated, are previously defined. The reagents and starting materials are readily available to one of ordinary skill in the art.

Scheme IX $RHNCO(CH_2)_{m-1}NTs(CH_2)_{n-1}CONHR$    27

| Step A
| Reduction

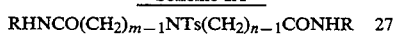

$RHN(CH_2)_mNTs(CH_2)_nNHR$    36

| Step B
| N-Akylation

$RN(CH_2)_mNTs(CH_2)_nNR$
|                                |
$HS(CH_2)_2$         $HS(CH_2)_2$

| Step C
| Deprotection

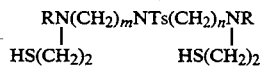

-continued
Scheme IX $RN(CH_2)_mNH(CH_2)_nNR$    38
|                               |
$HS(CH_2)_2$         $HS(CH_2)_2$

| Optional Step D

$RN(CH_2)_mNH(CH_2)_nNR$    39
|                               |
$H_2O_3PS(CH_2)_2$    $H_2O_3PS(CH_2)_2$

In Scheme IX, step A the appropriately substituted diamide (27), prepared in Scheme VI, step C is reduced to the triamine described by structure (36) under conditions well known in the art.

For example the diamide (27) is dissolved in a suitable organic solvent, such as tetrahydrofuran and treated with 2 equivalents of borane (1M solution in tetrahydrofuran) at 0° C. It is then stirred for 18 hours at reflux to provide the triamine (36) after isolation and purification by techniques that are well known in the art.

In step B the triamine (36) is di-N-alkylated with ethylene sulfide to provide the appropriately substituted di-N-alkylated triamine described by structure (37).

For example, the triamine (36) is dissolved in a suitable organic solvent, such as benzene and then treated with 2 equivalents of ethylene sulfide for 2 to 10 hours at a temperature of from room temperature to reflux to provide the di-N-alkylated triamine (37).

In step C the di-N-alkylated triamine (37) is deprotected under conditions well known in the art to provide the deprotected triamine described by structure (38).

For example, the di-N-alkylated triamine (37) is dissolved in a suitable organic solvent, such as 1,2-dimethoxylethane and treated with 4 equivalents of a suitable reducing agent, such as lithium aluminum hydride. The reaction is heated to reflux for about 18 hours. The reaction is then quenched by addition of water:10% sodium hydroxide:water in the ratio of 1.0:1.5:3.0 by volume where the first addition of water is equivalent to the amount of lithium aluminum hydride used by weight. The product is then isolated by extractive and purification techniques that are well known in the art to provide the deprotected triamine (38).

Alternatively, the di-N-alkylated triamine (37) can be deprotected following generally the procedure described in European Patent Application No. 349 224, published Mar. 1, 1990. The di-N-alkylated triamine (37) is dissolved in dry tetrahydrofuran, cooled to $-78°$ C. and treated with excess condensed ammonia. Excess sodium is added slowly at $-78°$ C. and the reaction is stirred for approximately 4 hours. It is then warmed to room temperature overnight with evaporation of the ammonia. Diethyl ether is added followed by the cautious addition of ethanol followed by water to finally quench the reaction. The solvents are removed under vacuum and the residue extracted with diethyl ether and chloroform. The combined extracts are dried over anhydrous sodium sulfate, filtered and concentrated under vacuum. The residue is purified by techniques well known in the art such as flash chromatography to provide the deprotected triamine (38).

In step optional step D the thiol functionalities of the deprotected triamine (38) may be converted to the corresponding phosphorothioates of structure (39).

For example, the appropriately substituted deprotected triamine (38) is treated with 4 equivalents of triethyl phosphite and 2 equivalents of bromotrichloromethane. The reaction is stirred for from one to three hours at a temperature range of from room temperature to reflux. The corresponding intermediate bis(diethylphosphorothioate) is recovered from the reaction by removal of the volatiles under vacuum and purification by flash chromatography. The intermediate bis(diethylphosphorothioate) is then cleaved by treatment with excess trimethylsilyl bromide. The reactants are contacted in a suitable organic solvent such as methylene chloride for about 2 to 24 hours at a temperature range of from room temperature to reflux. The volatiles are then removed under vacuum and the residue purified by techniques well known in the art to provide the phosphorothioates of structure (39).

The following examples represent typical syntheses of the compounds of formula (II) as described by Schemes VI, VII, VIII and IX. These examples are illustrative only and are not intended to limit the invention in any way. The reagents and starting materials are readily available to one of ordinary skill in the art. As used in the following examples, the following terms have the meanings indicated: "eq." refers to equivalents, "g" refers to grams, "mg" refers to milligrams, "mmol" refers to millimoles, "mL" refers to milliliters, "°C." refers to degrees Celsius, "TLC" refers to thin layer chromatography, "$R_f$" refers to retention factor and "$\delta$" refers to parts per million down field from tetramethylsilane.

EXAMPLE 9

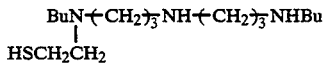

Preparation of 2-{Butyl-[3-(3-butylaminopropylamino)-propyl]-amino}-ethanethiol.

Scheme VI, step A; Dissolve β-alanine (10 mmol) in 10% sodium hydroxide and cool to 0° C. Add p-toluenesulfonyl chloride (10 mmol) dropwise to the solution. After 1 hour allow the reaction to warm to room temperature and stir for 2 days. Neutralize the reaction with 0.5N hydrochloric acid and extract with methylene chloride (3×50 mL). Combine the organic extracts, rinse with water (75 mL), brine (75 mL), dry over anhydrous sodium sulfate, filter and concentrate under vacuum to provide 3-(toluene-4-sulfonylamino)-propionic.

Scheme VI, step B; Dissolve 3-(toluene-4-sulfonylamino)-propionic (20 mmol) prepared in Scheme VI, step A in tetrahydrofuran (50 mL) and add butylamine (20 mmol). Add N-ethoxycarbonyl-2-ethoxy-1,2-dihydroquinoline (EEDQ) (22 mmol). Stir the reaction for 6 to 7 hours at room temperature and then concentrate under vacuum. Purify the residue by flash chromatography (silica gel, methanol/methylene chloride) to provide N-butyl-3-(toluene-4-sulfonylamino)-propionamide.

Alternatively N-butyl-3-(toluene-4-sulfonylamino)-propionamide can be prepared in Scheme VI, step B by dissolving 3-(toluene-4-sulfonylamino)-propionic (20 mmol) prepared in Scheme VI, step A in tetrahydrofuran (50 mL) followed by addition of N-methylmorpholine (20 mmol). Cool the reaction to −20° C. and add isobutyl chloroformate (20 mmol). Stir the reaction for 30 minutes and add butylamine (20 mmol) dissolved in dimethylformamide (5 mL). Stir the reaction for 2 hours at −20° C. and then warm to room temperature. Dilute the reaction with water (150 mL) and extract with diethyl ether (3×75 ml). Combine the organic extracts, dry over anhydrous magnesium sulfate, filter and concentrate under vacuum. Purify the residue by flash chromatography (silica gel, methanol/methylene chloride) to provide N-butyl-3-(toluene-4-sulfonylamino)-propionamide.

Scheme VI, step C; Dissolve N-butyl-3-(toluene-4-sulfonylamino)-propionamide (10 mmol) prepared in Scheme VI, step B in tetrahydrofuran (50 mL) and treat with sodium hydride (10 mmol). Stir the reaction for 30 minutes and add 3-bromo-N-butyl-propionamide (10 mmol) [prepared from amidation between Br(CH$_2$)$_2$CO$_2$H and butyl amine under conditions well known in the art as previously described generally]. Heat the reaction to reflux for 5 hours. After cooling dilute the reaction with methylene chloride (150 mL), rinse with water (100 mL), brine (100 mL), dry over sodium sulfate, filter and concentrate under vacuum. Purify the residue by flash chromatography (silica gel, methanol/methylene chloride) to provide N-butyl-3-[(2-butylcarbamoyl-ethyl)-(toluene-4-sulfonyl)-amino]-propionamide.

Scheme VII, step A; Dissolve N-butyl-3-[(2-butylcarbamoyl-ethyl)-(toluene-4-sulfonyl)-amino]-propionamide (10 mmol) prepared in Scheme VI, step C in tetrahydrofuran (50 mL). Cool the solution to 0° C. and add borane (10 mmol, 1M solution in tetrahydrofuran. Heat the reaction to reflux for 18 hours. After cooling, dilute the reaction with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide N-butyl-3-[(3-butylamino-propyl)-toluene-4-sulfonyl)-amino]-propionamide.

Scheme VII, step B; Dissolve N-butyl-3-[(3-butylamino-propyl)-toluene-4-sulfonyl)-amino]-propionamide (10 mmol) prepared in Scheme VII, step A in tetrahydrofuran (50 mL) and add dropwise ethylene sulfide (10 mmol). Heat the reaction to reflux for 4 hours. After cooling, concentrate the reaction under vacuum and purify the residue by flash chromatography (silica gel, methanol/methylene chloride) to provide 3-(benzenesulfonyl-{3-[butyl-(2-mercapto-ethyl)-amino]-propyl}-amino)-N-butyl-proponamide.

Scheme VII, step C; Dissolve 3-(benzenesulfonyl-{3-[butyl-(2-mercapto-ethyl)-amino]-propyl}-amino)-N-butyl-proponamide (10 mmol) prepared in Scheme VII, step B in 1,2-dimethoxyethane (50 mL) and treat with lithium aluminum hydride (20 mmol). Heat the re action to reflux for 18 hours. After cooling the react ion is worked up by consecutive addition of water (0.8 mL), 10% sodium hydroxide (1.2 mL) and water (2 .2 mL). Then dilute with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the title compound.

EXAMPLE 10

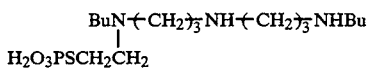

Preparation of 5,9,13-triaza-5-[(2-thiophosphoryl)ethyl]heptadecane.

Scheme VII, optional step D; Treat 2-{Butyl-[3-(3-butylamino-propylamino)-propyl]-amino}-ethanethiol (10 mmol) prepared in example 9 with triethyl phosphite (20 mmol) and bromotrichloromethane (10 mmol). Stir the reaction for 2 hours at reflux. Concentrate the reaction under vacuum and purify the the intermediate diethylphosphorothioate by flash chromatography (silica gel, ethyl acetate). The purified diethylphosphorothioate is then dissolved in methylene chloride (50 mL) and treated with excess trimethylsilyl bromide. Stir the reaction for 4 hours at −20° C. Concentrate the reaction under vacuum. Dissolve the residue in 2-propanol, add hydrochloric acid and collect the title compound by filtration as the hydrochloride salt.

EXAMPLE 11

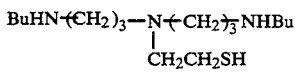

Preparation of 2-[Bis-(3-butylamino-propyl)-amino]-ethanethiol.

Scheme VI, step D; Dissolve N-butyl-3-[(2-butylcarbamoyl-ethyl)-toluene-4-sulfonyl)-amino]-propionamide (10 mmol) prepared in example 9 Scheme VI, step C in dry tetrahydrofuran (50 mL) and cool the solution to −78° C. Add excess dry ammonia followed by excess sodium. Stir the reaction for 4 hours and then warm to room temperature overnight. Add diethyl ether (100 mL) followed by cautious addition of ethanol (30 mL). After stirring for 30 minutes cautiously add water dropwise (5 mL) and then concentrate the reaction under vacuum. Extract the residue with diethyl ether (100 mL) and chloroform (100 mL). Combine the organic extracts, dry over anhydrous sodium sulfate, filter and concentrate under vacuum. Purify the residue by flash chromatography (silica gel, methanol/methylene chloride) to provide N-butyl-3-(2-butylcarbamoyl-ethylamino)-propionamide.

Scheme VIII, step A; Dissolve N-butyl-3-(2-butylcarbamoyl-ethylamino)-propionamide (10 mmol) prepared in Scheme VI, step D in tetrahydrofuran (50 mL) and add dropwise ethylene sulfide (22 mmol). Heat the reaction to reflux for 4 hours. After cooling, concentrate the reaction under vacuum and purify the residue by flash chromatography (silica gel, methanol/methylene chloride) to provide N-butyl-3-[(2-butylcarbamoyl-ethyl)-(2-mercapto-ethyl)amino]-propionamide.

Scheme VIII, step B; Dissolve N-butyl-3-[(2-butylcarbamoyl-ethyl)-(2-mercapto-ethyl)-amino]-propionamide (10 mmol) prepared in Scheme VIII, step A in 1,2-dimethoxyethane (50 mL) and treat with lithium aluminum hydride (20 mmol). Heat the reaction to reflux for 18 hours. After cooling the reaction is worked up by consecutive addition of water (0.8 mL), 10% sodium hydroxide (1.2 mL) and water (2.2 mL). Then dilute with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide the title compound.

EXAMPLE 12

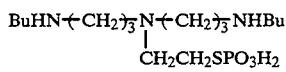

Preparation of 5,9,13-triaza-9-[(2-thiophosphoryl)ethyl]-heptadecane.

Scheme VIII, optional step C; Treat 2-[Bis-(3-butylamino-propyl)-amino]-ethanethiol (10 mmol) prepared in example 11 with triethyl phosphite (20 mmol) and bromotrichloromethane (10 mmol). Stir the reaction for 2 hours at reflux. Concentrate the reaction under vacuum and purify the the intermediate diethylphosphorothioate by flash chromatography (silica gel, ethyl acetate). The purified diethylphosphorothioate is t hen dissolved in methylene chloride (50 mL) and treated with excess trimethylsilyl bromide. Stir the reaction for 4 hours at −20° C. Dissolve the residue in 2-propanol, add hydrochloric acid and collect the title compound by filtration as the the hydrochloride salt.

EXAMPLE 13

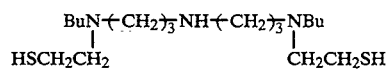

Preparation of 2-[Butyl-(3-{3-[butyl-(2-mercaptoethyl)-amino]-propylamino}-propyl)-amino]-ethanethiol.

Scheme IX, step A; Dissolve N-butyl-3-[(2-butylcarbamoyl-ethyl)-(toluene-4-sulfonyl)-amino]-propionamide (10 mmol) prepared in example 9, Scheme VI, step C in tetrahydrofuran (50 mL). Cool the solution to 0° C. and add borane (20 mmol, 1M solution in tetrahydrofuran. Heat the reaction to reflux for 18 hours. After cooling, dilute the reaction with methylene chloride (200 mL), rinse with water (100 mL), brine (100 mL), dry over anhydrous sodium sulfate, filter and concentrate under vacuum. Purify the residue by flash chromatography (silica gel, methanol/methylene chloride) to provide N,N-bis-(3-butylamino-propyl)-4-methyl-benzenesulfonamide.

Scheme IX, step B; Dissolve N,N-bis-(3-butylamino-propyl)-4-methyl-benzenesulfonamide (10 mmol) prepared in Scheme IX, step A in tetrahydrofuran (50 mL) and add dropwise ethylene sulfide (20 mmol). Heat the reaction to reflux for 4 hours. After cooling, concentrate the reaction under vacuum and purify the residue by flash chromatography (silica gel, methanol/methylene chloride) to provide N,N-bis-{3-[butyl-(2-mercapto-ethyl)-amino]-propyl}-4-methylbenzenesulfonamide.

Scheme IX, step C; Dissolve N,N-bis-{3-[butyl-(2-mercapto-ethyl)-amino]-propyl}-4-methyl-benzenesulfonamide (10 mmol) prepared in Scheme IX, step B in dry tetrahydrofuran (50 mL) and cool the solution to −78° C. Add excess dry ammonia followed by excess sodium. Stir the reaction for 4 hours and then warm to room temperature overnight. Add diethyl ether (100 mL) followed by cautious addition of ethanol (30 mL). After stirring for 30 minutes cautiously add water dropwise (5 mL) and then concentrate the reaction under vacuum. Extract the residue with diethyl ether (100 mL) and chloroform (100 mL). Combine the organic extracts, dry over anhydrous sodium sulfate, filter and concentrate under vacuum. Purify the residue by flash chromatography (silica gel, methanol/methylene chloride) to provide the title compound.

EXAMPLE 14

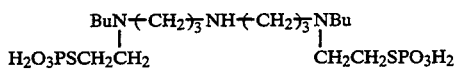

Preparation of 5,9,13-triaza-5,9-bis[(2-thiophosphoryl)ethyl]-heptadecane.

Scheme IX, optional step D; Treat 2-[Butyl-(3-{3-[butyl-(2-mercapto-ethyl)-amino]-propylamino}-propyl)-amino]ethanethiol (10 mmol) prepared in example 13 with triethyl phosphite (40 mmol) and bromotrichloromethane (20 mmol). Stir the reaction for 2 hours at reflux. Concentrate the reaction under vacuum and purify the the intermediate bis(diethylphosphorothioate) by flash chromatography (silica gel, ethyl acetate). The purified bis(diethylphosphorothioate) is then dissolved in methylene chloride (50 mL) and treated with excess trimethylsilyl bromide. Stir the reaction for 4 hours at −20° C. Dissolve the residue in 2-propanol, add hydrochloric acid and collect the title compound by filtration as the the hydrochloride salt.

The present invention provides a method of protecting cells from deleterious cellular effects caused by exposure to ionizing radiation or by exposure to a DNA-reactive agent.

Ionizing radiation is high energy radiation, such as an X-ray or a gamma ray, which interacts to produce ion pairs in matter. Exposure to ionizing radiation may occur as the result of environmental radiation, such as resulting from a nuclear explosion, a spill of radioactive material, close proximity to radioactive material and the like. More commonly, exposure to ionizing radiation may occur as the result of radiological medical procedures such as radiation therapy for various types of cancers.

DNA-reactive agents are those agents, such as alkylating agents, cross-linking agents, and DNA intercalating agents, which interact covalently or non-covalently with cellular DNA causing certain deleterious cellular effects. For example, DNA-reactive agents include cisplatin, cyclophosphamide, diethylnitrosoamine, benzo(a)pyrene, carboplatin, doxorubicin, mitomycin-C and the like. Many of these DNA-reactive agents, such as cisplatin, cyclophosphamide, doxorubicin and mitomycin-C are useful in cancer therapy as DNA-reactive chemotherapeutic agents.

Deleterious cellular effects caused by exposure to ionizing radiation or to a DNA-reactive agent include damage to cellular DNA, such as DNA strand break, disruption in cellular function, such as by disrupting DNA function, cell death, tumor induction, such as therapy-induced secondary tumor induction, and the like. These deleterious cellular effects can lead to secondary tumors, bone marrow suppression, kidney damage, peripheral nerve damage, gastrointestinal damage and the like. For example, in cancer radiation therapy, the exposure to radiation is intended to cause cell death in the cancer cells. Unfortunately, a large part of the adverse events associated with the therapy is caused by these deleterious cellular effects of the radiation on normal cells as opposed to cancer cells.

The present invention provides a method by which cells are protected from deleterious cellular effects by preventing or eliminating these effects or by reducing their severity. According to the present invention, the cells to be protected are contacted with a compound of formula (I) or (II) prior to or during exposure of the cell to ionizing radiation or to DNA-reactive agents. The cells may be contacted directly, such as by applying a solution of a compound of the invention to the cell or by administering a compound of the invention to a mammal. The compounds of the present invention thus provide a protective effect in the cell which eliminates or reduces the severity of the deleterious cellular effects which would otherwise be caused by the exposure.

More particularly, the present invention provides a method of protecting non-cancer, or normal, cells of a mammal from deleterious cellular effects caused by exposure of the mammal to ionizing radiation or to a DNA-reactive agent. As used herein, the term "mammal" refers to warmblooded animals such as mice, rats, dogs and humans. The compounds of the present invention provide a selective protection of normal cells, and not of cancer cells, during cancer radiation therapy and during chemotherapy with a DNA-reactive chemotherapeutic agent. According to the present invention the compound of the invention is administered to the mammal prior to or during exposure to ionizing radiation or to a DNA-reactive agent. The present invention provides a method whereby the deleterious cellular effects on non-cancer cells caused by exposure of the mammal to ionizing radiation or to a DNA-reactive agent are eliminated or reduced in severity or in extent.

In addition, the present invention provides a method of treating a patient in need of radiation therapy or in need of chemotherapy with a DNA-reactive chemotherapeutic agent. As used herein, the term "patient" refers to a mammal, including mice, rats, dogs and humans, which is afflicted with a neoplastic disease state or cancer such that it is in need of cancer radiation therapy or chemotherapy with a DNA-reactive chemotherapeutic agent. The term "neoplastic disease state" as used herein refers to an abnormal state or condition characterized by rapidly proliferating cell growth or neoplasm.

Neoplastic disease states for which treatment with a compound of formula (I) or (II) will be particularly useful in conjunction with radiation therapy or chemotherapy with a DNA-reactive chemotherapeutic agent include: Leukemias such as, but not limited to, acute lymphoblastic, acute myelogenous, chronic lymphocytic, acute myeloblastic and chronic myelocytic; Carcinomas, such as, but not limited to, those of the cervix, esophagus, stomach, pancreas, breast, ovaries, small intestines, colon and lungs; Sarcomas, such as, but not limited to, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma, Hodgkin's disease and non-Hodgkin's lymphoma. Neoplastic disease states for which treatment with a compound of formula (I) or (II) will be particularly preferred in conjunction with radiation therapy or chemotherapy include Hodgkin's disease, pancreatic carcinoma, advanced carcinoma, breast cancers, ovarian cancer, colon cancers and the like.

In addition, treatment with a compound of the present invention provides selective protection against deleterious cellular effects, such as therapy-induced secondary tumor induction, caused by radiation therapy or chemotherapy with a DNA-reactive chemotherapeutic agent. Treatment with a compound of the present invention is thus useful in eliminating or reducing the risk of secondary tumor induction, such as therapy-induced acute myelogenous leukemia and non-Hodgkin's lymphoma, brought about by radiotherapy or chemotherapy for treatment of Hodgkin's disease.

According to the present invention, administration to a patient of a compound of formula (I) or (II) prior to or during radiation therapy or chemotherapy with a DNA-reactive chemotherapeutic agent will provide a selective protection of non-cancer cells of the patient but not of cancer cells. The deleterious cellular effects on non-cancer cells caused by treatment of the patient with ionizing radiation or with a DNA-reactive chemotherapeutic agent are thus eliminated or reduced in severity or in extent.

A protective amount of a compound of formula (I) or (II) refers to that amount which is effective, upon single or multiple dose administration to a mammal or patient, in eliminating or reducing in severity or in extent the deleterious cellular effects caused by exposure to or treatment with ionizing radiation or a DNA-reactive agent. A protective amount of a compound of formula (I) or (II) also refers to that amount which is effective, upon single or multiple dose administration to the cell, in eliminating or reducing in severity or in extent the deleterious cellular effects caused by exposure to ionizing radiation or a DNA-reactive agent.

A protective amount for administration to a mammal or a patient can be readily determined by the attending diagnostician, as one skilled in the art, by the use of known techniques and by observing results obtained under analogous circumstances. In determining the protective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

The compounds of formula (I) or (II) may be administered as single doses or as multiple doses and are ordinarily administered prior to and/or during exposure to ionizing radiation or to DNA-reactive agents. Generally, where a compound of the present invention is administered in conjunction with radiation therapy, the compound of the present invention will be administered in single or multiple doses prior to radiation therapy following a schedule calculated to provide the maximum selective protective effect during radiation therapy. Generally, where a compound of the present invention is administered in conjunction with a DNA-reactive chemotherapeutic agent, the compound of the present invention will be administered in single or multiple doses prior to and during chemotherapy following a schedule calculated to provide the maximum selective protective effect during chemotherapy.

The details of the dosing schedule for the compounds of the present invention necessary to provide the maximum selective protective effect upon exposure to ionizing radiation or to a DNA-reactive agent can be readily determined by an attending physician, as one skilled in the art, by the use of known techniques and by observing results obtained under analogous circumstances.

A protective amount of a compound of formula (I) or (II) for administration to a mammal or patient will vary from about 5 milligram per kilogram of body weight per day (mg/kg/day) to about 1000 mg/kg/day. Preferred amounts are expected to vary from about 50 to about 500 mg/kg/day.

A protective amount of a compound of formula (I) or (II) for contacting a cell will vary from about 100 micromolar to about 5 millimolar in concentration.

A compound of formula (I) or (II) can be administered to a mammal or a patient in any form or mode which makes the compound bioavailable in effective amounts, including oral and parenteral routes. For example, compounds of formula (I) and (II) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (I) or (II) in admixture or otherwise in association with one or more inert carriers. These compositions are useful, for example, as assay standards, as convenient means of making bulk shipments, or as pharmaceutical compositions. An assayable amount of a compound of formula (I) or (II) is an amount which is readily measurable by standard assay procedures and techniques as are well known and appreciated by those skilled in the art. Assayable amounts of a compound of formula (I) or (II) will generally vary from about 0.001% to about 75% of the composition by weight. Inert carriers can be any material which does not degrade or otherwise covalently react with a compound of formula (I) or (II). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (I) or (II) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel TM, corn starch and the like; lubricants such as magnesium stearate or Sterotex TM; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (I) or (II) in their end-use application.

Compounds of formula (I) wherein R is ethyl, propyl or butyl are generally preferred. Compounds of formula (I) wherein m is 2 or 3 are generally preferred. Compounds of formula (I) wherein n is 7 or 8 are generally preferred.

Compounds of formula (II) wherein R is ethyl, propyl or butyl are generally preferred. Compounds of formula (II) wherein m is 3 or 4 are generally preferred. Compounds of formula (II) wherein n is 3 are generally preferred.

The utility of the compounds of the present invention may be demonstrated as radioprotective agents both in vitro and in vivo.

For example, the ability of cultured cells to form clones (colonies) may be evaluated as a function of exposure to X-ray dose or chemical dose. Cells are either not drug treated or are treated with a test agent 30 minutes prior to exposure. The degree of retention of ability to form clones after exposure, in comparison to untreated cells, is directly related to the protective effect of the drug. A typical experiment of this type may be carried out essentially as described by Snyder and Lachmann [*Radiation Res.* 120, 121 (1989)].

Alternatively, the production of DNA strand breaks upon exposure to X-ray dose or chemical dose may be evaluated. Cells are either not drug treated or are treated with a test agent about 30 minutes prior to exposure. The extent of DNA strand breakage after exposure, in comparison to that in untreated cells, is inversely related to the protective effect of the drug. A typical experiment of this type may be carried out essentially as described by Snyder [*Int. J. Radiat. Biol.* 55, 773 (1989)].

In addition, the survivability of mice exposed to whole body irradiation or to a DNA-reactive agent may be evaluated. Animals, either pre-treated with a test agent or untreated (Control Group), are exposed to whole body irradiation (1500 rads). Untreated control animals are expected to survive about 12–15 days. The degree of survivability of the treated animals, in comparison to the untreated controls, is directly related to the protective effect of the drug treatment. A typical experiment of this type may be carried out essentially as described by Carroll et al. [*J. Med. Chem.* 33, 2501 (1990)].

The production of DNA strand breaks in lymphocytes taken from treated animals exposed to whole body irradiation or to a DNA-reactive agent may be evaluated in comparison to untreated control. Alternatively, the viability and clonogenicity of bone marrow cells taken from treated animals exposed to whole body irradiation or to a DNA-reactive agent may be evaluated in comparison to untreated control as described by Pike and Robinson [*J. Cell Physiol.* 76, 77 (1970)].

What is claimed is:

1. A compound of the formula

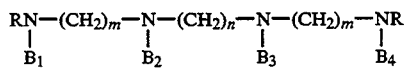

wherein m is an integer from 2 to 4,
n is an integer from 4 to 10,
R is $C_2$-$C_6$ alkyl and
$B_1$, $B_2$, $B_3$ and $B_4$ are each independently H, —$CH_2CH_2SH$ or —$CH_2CH_2SPO_3H_2$,
with the proviso that at least one of $B_1$, $B_2$, $B_3$ or $B_4$ is other than H.

2. A compound of the formula

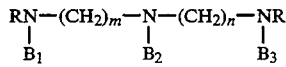

wherein
m is an integer from 2 to 4,
n is an integer from 3 to 10,
R is $C_2$-$C_6$ alkyl and
$B_1$, $B_2$ and $B_3$ are each independently H, —$CH_2CH_2SH$ or —$CH_2CH_2SPO_3H_2$,
with the proviso that at least one of $B_1$, $B_2$ or $B_3$ is other than H.

3. A compound according to claim 1 wherein m is 2.
4. A compound according to claim 1 wherein m is 3.
5. A compound according to claim 1 wherein n is 7.
6. A compound according to claim 1 wherein n is 8.
7. A compound according to claim 3 wherein n is 7.
8. A compound according to claim 4 wherein n is 7.
9. A compound according to claim 2 wherein m is 3.
10. A compound according to claim 2 wherein m is 4.
11. A compound according to claim 2 wherein n is 3.
12. A compound according to claim 11 wherein m is 3.
13. A compound according to claim 11 wherein m is 4.
14. A method of protecting mammalian cells from deleterious cellular effects caused by exposure to ionizing radiation comprising contacting said cells with a protective amount of a compound of claim 1 or 2.
15. A method of protecting mammalian cells from deleterious cellular effects caused by exposure to a DNA-reactive agent comprising contacting said cells with a protective amount of a compound of claim 1 or 2.
16. A method of protecting non-cancer cells of a human from deleterious cellular effects caused by exposure to ionizing radiation comprising administering to said human a protective amount of a compound of claim 1 or 2.
17. A method of protecting non-cancer cells of a human from deleterious cellular effects caused by exposure to a DNA-reactive agent comprising administering to said human a protective amount of a compound of claim 1 or 2.
18. A method of treating a patient in need of radiation therapy comprising administering to said patient a protective amount of a compound of claim 1 or 2.
19. A method of treating a patient in need of chemotherapy with a DNA-reactive chemotherapeutic agent comprising administering to said patient a protective amount of a compound of claim 1 or 2.

* * * * *

UNITED STATES PATENT AND TRADEMARK OFFICE
CERTIFICATE OF CORRECTION

PATENT NO. : 5,434,145
DATED : July 18, 1995
INVENTOR(S) : Michael L. Edwards, et al.

Page 1 of 2

It is certified that error appears in the above-identified patent and that said Letters Patent is hereby corrected as shown below:

At Column 4, line 68, the patent reads "rosylate" and should read --tosylate--.
At Column 6, line 15, the patent reads "the extracted" and should read --then extracted--.
At Column 9, line 3, the patent reads "RTN($CH_2$)" and should read --RHN($CH_2$)--.
At Column 14, line 61, the patent reads "the the" and should read --the--.
At Column 15, line 8, the patent reads "actyl" and should read --octyl--.
At Column 16, line 1, the patent reads "the the" and should read --the--.
At Column 17, line 3, the patent reads "the the" and should read --the--.
At Column 18, line 20, the patent reads "the the" and should read --the--.
At Column 21, line 35, the patent reads "with equivalent" and should read --with 1 equivalent--.
At Column 23, line 2, the patent reads "dimethoxylethane" and should read --dimethoxyethane--.
At Column 25, line 1, the patent reads "In Step optional Step" and should read --In optional Step--.
At Column 26, line 53, the patent reads "proponamide" and should read --propionamide--.
At Column 26, line 59, the patent reads "re action" and should read --reaction--.
At Column 26, line 60, the patent reads "re action" and should read --reaction--.
At Column 27, line 14, the patent reads "the the" and should read --the--.

UNITED STATES PATENT AND TRADEMARK OFFICE
CERTIFICATE OF CORRECTION

PATENT NO. : 5,434,145
DATED : July 18, 1995
INVENTOR(S) : Michael L. Edwards, et al.

It is certified that error appears in the above-identified patent and that said Letters Patent is hereby corrected as shown below:

At Column 28, line 18, the patent reads "the the" and should read --the--.
At Column 28, line 25, the patent reads "the the" and should read --the--.
At Column 29, line 20, the patent reads "the the" and should read --the--.
At Column 29, line 27, the patent reads "the the" and should read --the--.
At Column 30, line 58, the patent reads "lymphold" and should read --lymphoid--.
At Column 33, line 58, the patent reads "include the one or more" and should read --include one or more--.

Signed and Sealed this

Twenty-eighth Day of May, 1996

BRUCE LEHMAN

*Attest:*

*Attesting Officer*   *Commissioner of Patents and Trademarks*